US00PP32668P2

(12) United States Plant Patent
Hooper

(10) Patent No.: US PP32,668 P2
(45) Date of Patent: Dec. 22, 2020

(54) *MAGNOLIA* PLANT NAMED 'MGYOD209A'

(50) Latin Name: ***Magnolia* hybrid**
Varietal Denomination: MGYOD209A

(71) Applicant: Vance James Hooper, Waitara (NZ)

(72) Inventor: Vance James Hooper, Waitara (NZ)

( * ) Notice: Subject to any disclaimer, the term of this patent is extended or adjusted under 35 U.S.C. 154(b) by 0 days.

(21) Appl. No.: 16/873,146

(22) Filed: Feb. 13, 2020

(51) Int. Cl.
*A01H 5/02* (2018.01)
*A01H 6/00* (2018.01)

(52) U.S. Cl.
USPC ..... Plt./223

(58) Field of Classification Search
USPC ..... Plt./223
CPC ..... A01H 5/02; A01H 5/00; A01H 6/00
See application file for complete search history.

*Primary Examiner* — June Hwu

(57) ABSTRACT

A new cultivar of *Magnolia* plant named 'MGYOD209A' that is characterized by a compact upright habit, medium sized leaves, flowers having tepals that are light purple on the upper surface, red-purple on the lower surface and then fade to pink on the lower surface and light pink on the upper surface and a large number of flowers during the Summer.

2 Drawing Sheets

Botanical classification: *Magnolia* hybrid.
Variety denomination: 'MGYOD209A'.

BACKGROUND OF THE INVENTION

The present invention relates to a new and distinct cultivar of *Magnolia* plant botanically known as *Magnolia* hybrid and hereinafter referred to by the cultivar name 'MGYOD209A'.

The new cultivar is the product of a breeding program conducted by the inventor in a cultivated area of Waitara, New Zealand. The objective of the breeding program is to develop new *Magnolia* cultivars that are smaller in size and have attractive flower colors.

'MGYOD209A' originated from crossing the female or seed parent *Magnolia* hybrid 'Star Wars' (not patented) and the male or pollen parent *Magnolia soulangeana* x *liliiflora* 'Genie' (U.S. Plant Pat. No. 20,748). The crossing was conducted in 2006 in a controlled environment. The cultivar 'MGYOD209A' was selected by the inventor in 2010 as a single plant within the progeny of the stated cross in a cultivated area of Waitara, New Zealand.

Asexual reproduction of the new cultivar 'MGYOD209A' by field budding was first performed in 2010 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Magnolia* cultivar 'MGYOD209A'. These traits in combination distinguish 'MGYOD209A' as a new and distinct cultivar.

1. *Magnolia* 'MGYOD209A' exhibits a compact upright habit.
2. *Magnolia* 'MGYOD209A' exhibits medium sized leaves.
3. *Magnolia* 'MGYOD209A' exhibits flowers having tepals that are light purple on the upper surface, red-purple on the lower surface and then fade to pink on the lower surface and light pink on the upper surface.
4. *Magnolia* 'MGYOD209A' exhibits a large number of flowers during the Summer.

The closest comparison variety is *Magnolia* 'Amethyst Flame' (not patented).

'MGYOD209A' is different than 'Amethyst Flame' in the following characteristics:

1. *Magnolia* 'MGYOD209A' exhibits a compact upright habit. In contrast, 'Amethyst Flame' has a broader less compact habit.
2. *Magnolia* 'MGYOD209A' exhibits medium sized leaves. In contrast, 'Amethyst Flame' has larger leaves.
3. *Magnolia* 'MGYOD209A' exhibits flowers having tepals that are light purple on the upper surface, red-purple on the lower surface and then fade to pink on the lower surface and light pink on the upper surface. In contrast, the flowers of 'Amethyst Flame' have tepals that are initially red-purple and then turn pale purple on both upper and lower surfaces.
4. *Magnolia* 'MGYOD209A' exhibits a large number of flowers during the Summer. In contrast, 'Amethyst Flame' produces a smaller number of flowers during the Summer.

'MGYOD209A' is different than the female parent plant in the following characteristics:

1. *Magnolia* 'MGYOD209A' exhibits a compact upright habit. In contrast, the female parent plant is larger in size and has a more rounded shape.
2. *Magnolia* 'MGYOD209A' exhibits medium sized leaves. In contrast, the female parent plant has larger leaves.
3. *Magnolia* 'MGYOD209A' exhibits flowers having tepals that are light purple on the upper surface, red-purple on the lower surface and then fade to pink on the lower surface and light pink on the upper surface. In contrast, the flowers of the female parent plant have tepals that are initially red-pink and then turn pale pink on the lower surface and white on the upper surface.

'MGYOD209A' is different than the male parent plant in the following characteristics:

1. *Magnolia* 'MGYOD209A' exhibits a compact upright habit. In contrast, the male parent plant has a wider pyramidal shape.
2. *Magnolia* 'MGYOD209A' exhibits flowers having tepals that are light purple on the upper surface, red-purple on the lower surface and then fade to pink on the lower surface and light pink on the upper surface. In contrast, the flowers of the male parent plant have tepals that are red on both surfaces.

BRIEF DESCRIPTION OF THE DRAWING

The accompanying photographs illustrate the distinguishing traits of *Magnolia* 'MGYOD209A'.

The photograph of FIG. 1 shows an overall view of a 1 year old plant in flower.

Figure 1:
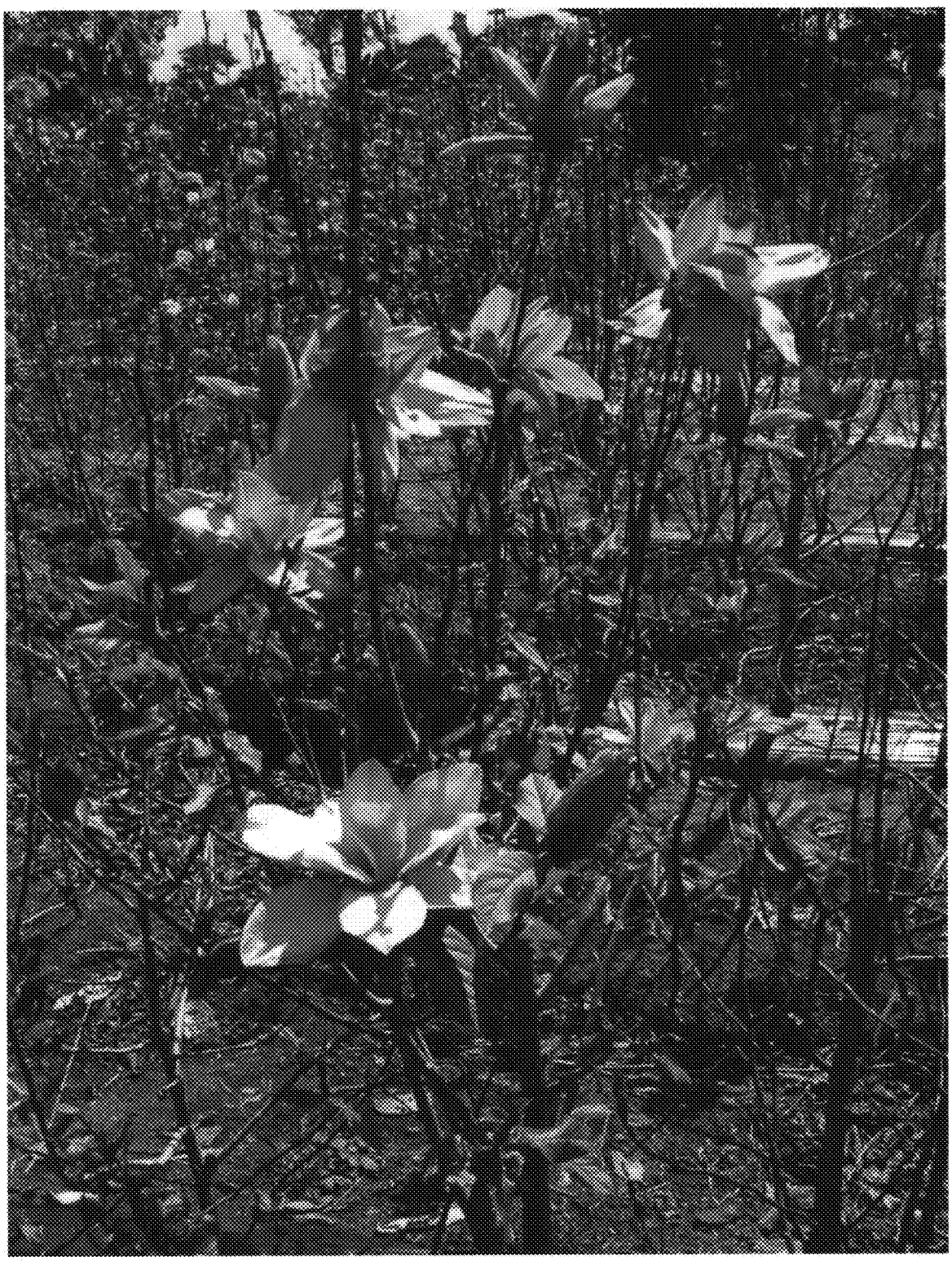
Figure 2:
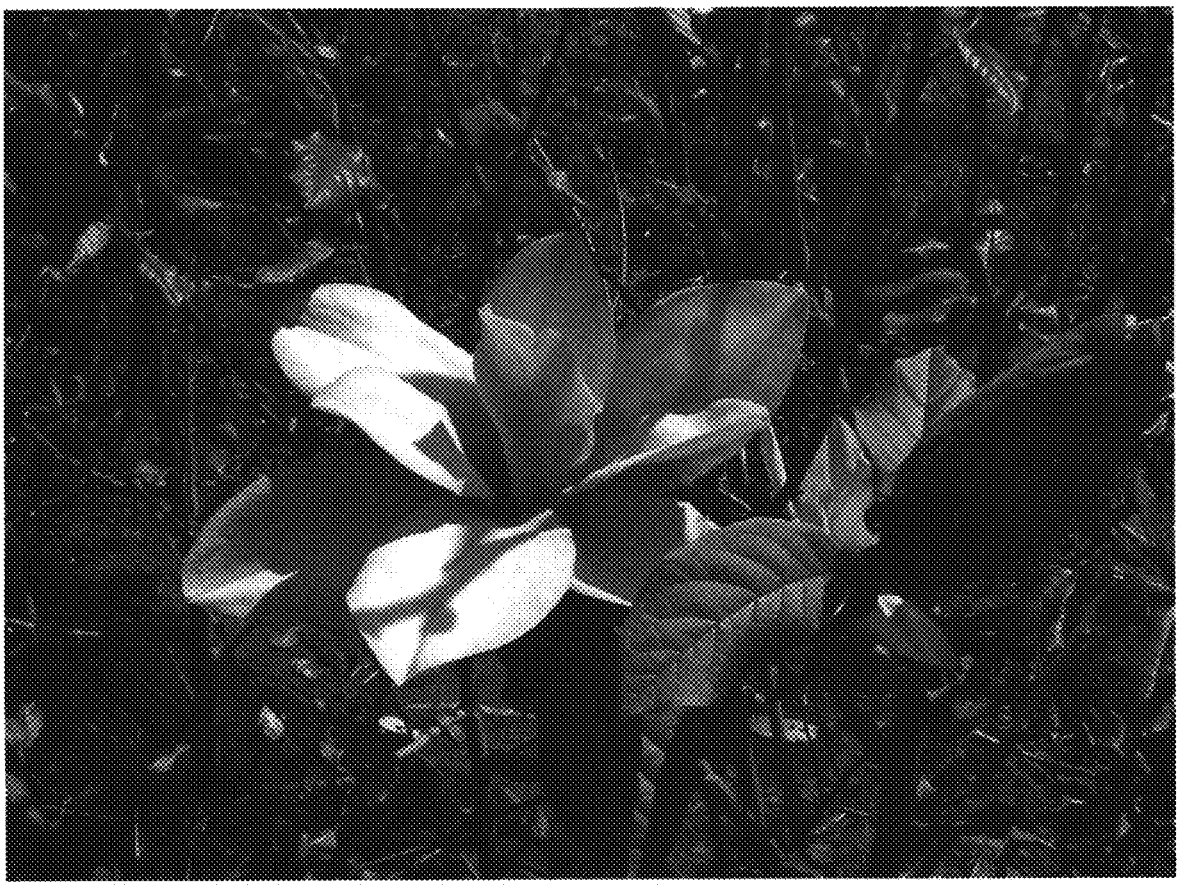

The photograph of FIG. 2 shows a close-up view of the flowers and foliage.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Magnolia* cultivar named 'MGYOD209A'. Data was collected in Waitara, New Zealand from 1 year old field grown plants. The time of year was Spring and the average temperature was 15° Centigrade during the day and 9° Centigrade at night. Color determinations are in accordance with The Royal Horticultural Society Colour Chart 2015 edition, except where general color terms of ordinary dictionary significance are used. The growing requirements are similar to the species. 'MGYOD209A' has not been tested under all possible conditions and phenotypic differences may be observed with variations in environmental, climatic, and cultural conditions, however, without any variance in genotype.

Botanical classification: *Magnolia* hybrid 'MGYOD209A'.
Use: Ornamental perennial.
Parentage: 'MGYOD209A' originated from the crossing of the female or seed parent *Magnolia* 'Star Wars' and the male or pollen parent *Magnolia* 'Genie'.
Container size: 10 liter.
Vigor: Moderate.
Plant type: Small tree.
Growth habit: Upright.
Plant shape: Slender, upright.
Height: 1.25 meters in height.
Width: 30 cm. in width.
Growth rate: 30 to 40 cm. per year.
Hardiness: −15° to 35° C.
Propagation: Field budding.
Crop time: 1 year from grafting.
Root: Fine and fibrous.
Stem:
- *Branching habit.*—Upright branching with branches less than 45 degrees from vertical.
- *Basal branching.*—Occasional.
- *Number of lateral branches.*—3 to 5.
- *Lateral branch diameter.*—6 to 8 mm. in diameter.
- *Lateral branch length.*—10 to 30 cm. in length.
- *Internode length.*—15 to 55 mm. between nodes.
- *Stem color.*—N199A in sun, 147B in shade.
- *Stem aspect.*—Upright.
- *Pubescence.*—Slight, only present on first 10 cm. from end of lateral branches.
- *Stem shape.*—Round.
- *Stem texture.*—Smooth.
- *Stem strength.*—Moderate.
- *Pinching.*—Not required.

Foliage:
- *Leaf arrangement.*—Alternate.
- *Compound or single.*—Single.
- *Quantity of leaves per lateral branch.*—4 to 8.
- *Leaf shape.*—Ovate to elliptical.
- *Leaf apex.*—Acute.
- *Leaf base.*—Acute.
- *Leaf length.*—12.0 to 15.0 cm. in length.
- *Leaf width.*—7.5 to 10.0 cm. in width.
- *Pubescence.*—Absent on upper surface, sparse hairs on lower surface of new leaves.
- *Leaf texture.*—Both surfaces leathery.
- *Leaf luster.*—Slightly glossy on both surfaces.
- *Leaf margin.*—Entire, slightly undulating.
- *Vein pattern.*—Pinnate.
- *Young leaf color (upper surface).*—146A.
- *Young leaf color (lower surface).*—147B.
- *Mature leaf color (upper surface).*—137A.
- *Mature leaf color (lower surface).*—NN137C.
- *Vein color (upper surface).*—137A.
- *Vein color (lower surface).*—138B.
- *Leaf attachment.*—Petiolate.
- *Petiole dimensions.*—10 to 20 mm. in length and 2 to 3 mm. in diameter.
- *Petiole color.*—148B.
- *Durability of foliage to stress.*—High.

Flower:
- *Flower arrangement.*—Solitary terminal open star shaped to cup and saucer shaped flowers.
- *Quantity of flowers per lateral stem.*—1 or 2.
- *Quantity of flower buds per lateral stem.*—1 or 2.
- *Quantity of flowers and buds per plant.*—Approximately 3 to 7.
- *Flowering habit.*—Flowers bloom in Spring before foliage appears and mid to late Summer with foliage.
- *Flowering season.*—Spring and mid to late Summer.
- *Time to flower or response time.*—5 to 7 weeks after breaking dormancy.
- *Fragrance.*—Slight fruity scent.
- *Self-cleaning or persistent.*—Self cleaning.
- *Flower bud length.*—20 to 35 mm. in length.
- *Flower bud diameter.*—10 to 15 mm. in diameter.
- *Flower bud shape.*—Cordate.
- *Rate of bud opening.*—10 to 14 days.
- *Bud color.*—N79B to N79C.
- *Flower aspect.*—Upright.
- *Flower shape.*—Star shaped.
- *Flower dimensions.*—18 to 20 cm. in diameter and 8 to 9 cm. in height.
- *Flower longevity.*—Lasts approximately 7 to 9 days on plant.
- *Flower longevity as a cut flower.*—Lasts approximately 5 to 6 days.
- *Tepal arrangement.*—Whorls of 3 or 4.
- *Number of tepals.*—9 to 12.
- *Fused or unfused.*—Not fused.
- *Tepal shape.*—Ovate.

*Tepal margin.*—Entire, slightly undulating.
*Tepal apex.*—Acute.
*Tepal base.*—Rounded.
*Tepal texture.*—Smooth both surfaces.
*Tepal luster.*—Slightly glossy both surfaces.
*Tepal dimensions.*—7.5 to 10.0 cm. in length and 5.5 to 6.5 cm. in width.
*Tepal color when opening* (*upper side*).—76B to 76C, veins 76B.
*Tepal color when opening* (*under side*).—64A to 64B.
*Tepal color when fully opened* (*upper side*).—76C to 76D.
*Tepal color when fully opened* (*under side*).—64C to 64D.
*Tepal color fading to* (*upper side*).—73B.
*Tepal color fading to* (*lower side*).—73A.

Sepals: Absent.

Peduncle:
*Peduncle dimensions.*—9 to 10 mm. in length and 6 to 8 mm. in diameter.
*Peduncle angle.*—Vertical.
*Peduncle strength.*—Strong.
*Peduncle pubescence.*—Covered with short adpressed hairs.
*Peduncle color.*—137D.

Reproduction organs:
*Stamen number.*—68 to 72.
*Anther shape.*—Curved upward.
*Anther length.*—14 to 15 mm. in length.
*Anther color.*—Inner side 73D, outer side 74B flushed 73B.
*Amount of pollen.*—Moderate.
*Pollen color.*—4D.
*Pistil number.*—40 to 42 in number.
*Pistil length.*—14 to 15 mm.
*Stigma shape.*—Curved out and upward.
*Stigma color.*—73D turning 186A to 186B.
*Ovary color.*—186A to 186B.

Fruit and seed production has not been observed to date.

Disease and pest resistance has not been observed to date.

The invention claimed is:

1. A new and distinct variety of *Magnolia* plant named 'MGYOD209A' as described and illustrated.

* * * * *